(12) United States Patent
Fenlin

(10) Patent No.: US 6,197,062 B1
(45) Date of Patent: Mar. 6, 2001

(54) MODULAR SHOULDER PROSTHESIS SYSTEM

(75) Inventor: John M. Fenlin, Bryn Mawr, PA (US)

(73) Assignee: Howmedica Osteonics, Corp., Allendale, NJ (US)

( * ) Notice: Subject to any disclaimer, the term of this patent is extended or adjusted under 35 U.S.C. 154(b) by 0 days.

(21) Appl. No.: 09/228,175

(22) Filed: Jan. 11, 1999

(51) Int. Cl.$^7$ ........................................ A61F 2/40
(52) U.S. Cl. ............................ 623/19.12; 623/19.13
(58) Field of Search ...................... 623/19.11, 19.12, 623/19.13, 19.14

(56) References Cited

U.S. PATENT DOCUMENTS

| | | | |
|---|---|---|---|
| 4,822,370 | * 4/1989 | Schelhas | 623/23 |
| 4,865,605 | 9/1989 | Dines et al. | 623/19 |
| 4,919,670 | 4/1990 | Dale et al. | 623/19 |
| 4,957,510 | * 9/1990 | Cremascoli | 623/23 |
| 4,963,155 | * 10/1990 | Lazzeri et al. | 623/23 |
| 5,080,685 | 1/1992 | Bolesky et al. | 623/23 |
| 5,135,529 | 8/1992 | Paxson et al. | 606/85 |
| 5,181,928 | 1/1993 | Bolesky et al. | 623/23 |
| 5,314,479 | 5/1994 | Rockwood, Jr. et al. | 623/19 |
| 5,358,526 | * 10/1994 | Tornier | 623/19 |
| 5,580,352 | * 12/1996 | Sekel | 623/23 |

FOREIGN PATENT DOCUMENTS

| | | | |
|---|---|---|---|
| 0257359 | 8/1987 | (EP) | A61F/2/36 |
| 0797964 | 10/1997 | (EP) | A61F/2/36 |
| 9846172 | 10/1998 | (WO) | A61F/2/40 |

OTHER PUBLICATIONS

4–page brochure; Tornier, Inc; Aequalis Glenoid Component.
4–page brochure; Tornier, Inc; The Aequalis™ Shoulder Prosthesis.
24–page brochure; DePuy; Total Shoulder Arthroplasty System; 1995.

* cited by examiner

Primary Examiner—David J. Isabella
(74) Attorney, Agent, or Firm—Volpe and Koenig, P.C.

(57) ABSTRACT

A shoulder prosthesis system including a plurality of connectors for interconnecting "standard" shoulder prosthesis stems with "standard" shoulder prosthesis heads. The connectors enable a selected stem to be interconnected with a selected head in a plurality of configurations having various tilt angles, and radial offsets and lengths.

13 Claims, 4 Drawing Sheets

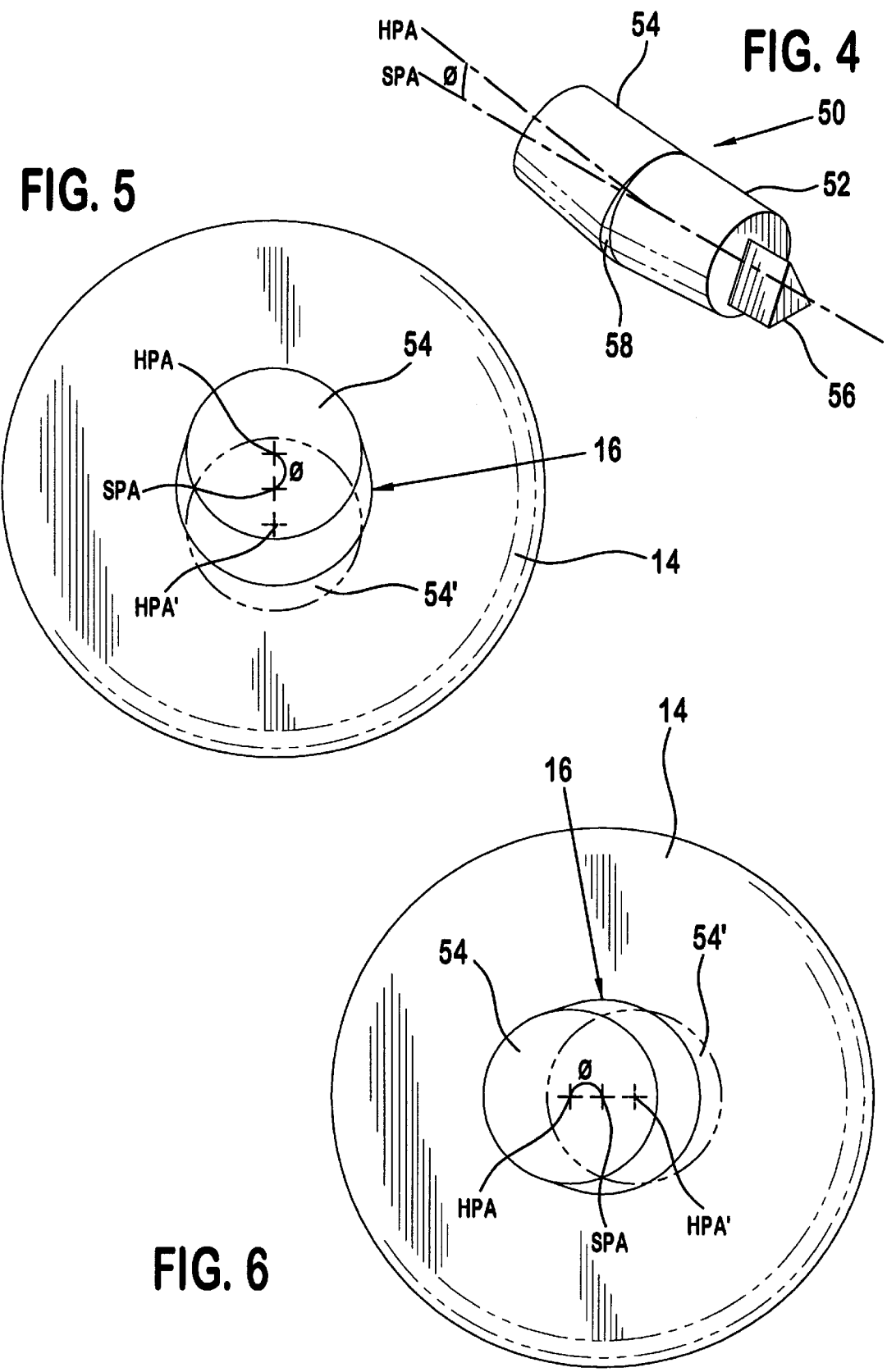

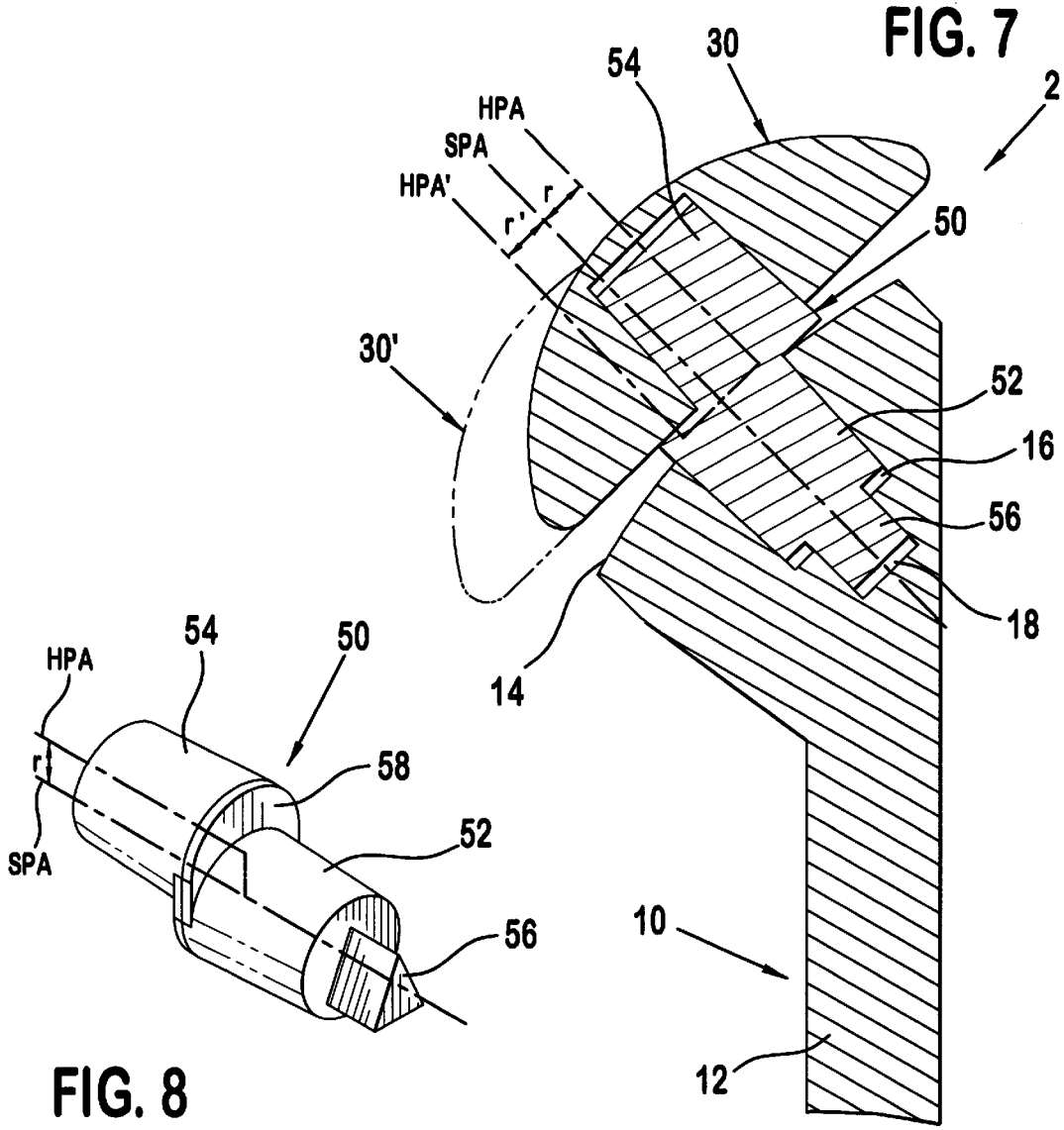
FIG. 7
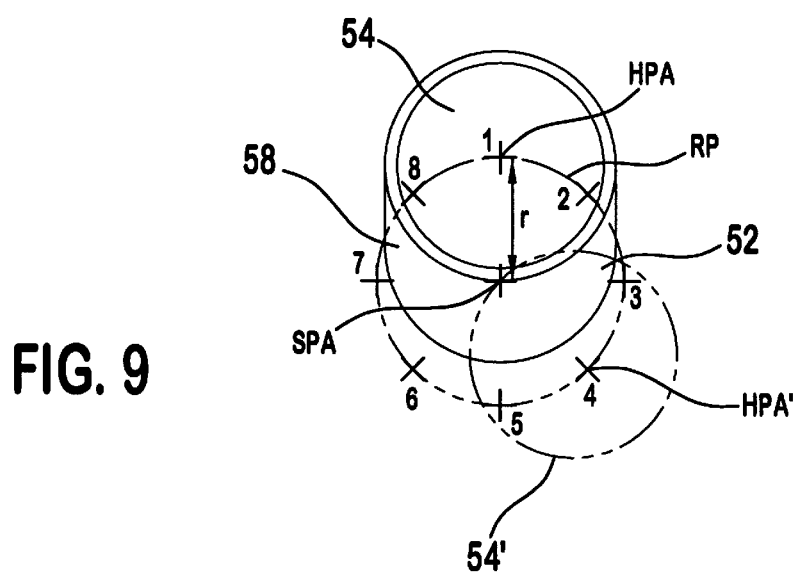
FIG. 8
FIG. 9

MODULAR SHOULDER PROSTHESIS SYSTEM

BACKGROUND OF THE INVENTION

1. Field of the Invention

The present invention relates to shoulder prostheses. More particularly, the present invention relates to a modular shoulder prosthesis system including connectors which allow standard prosthesis stems and heads to be interconnected in various configurations.

2. Description of the Prior Art

Early shoulder prostheses directly mimicked the upper portion of the humerus which they were designed to replace. That is, they were typically unitary structures including a stem, to be implanted within the humerus, and a head, to be positioned within the glenoid cavity of the scapula.

One problem with conventional unitary shoulder prostheses was the necessity of maintaining large inventories of differently configured prostheses to accommodate patients' differing anatomies. Not only were prostheses with different sizes of heads and stems required, but also prostheses with the head and stem configured at various tilt angles and radial offsets relative to one another. These various configurations were required in each size category.

To reduce the required inventory, assorted modular prostheses have been devised. Prior art modular systems have generally been designed to allow flexibility with respect to either the tilt angle or the radial offset between the head and stem. Although some of these prior art modular systems utilize either a "standard" head or a "standard" stem, most still require a plurality of either the heads or the stems to provide complete tilt angle and radial offset flexibility. None of the prior art systems provides complete tilt angle and radial offset flexibility without requiring different modular head or stem components of each given size. As a result, substantial inventories of either the stems or heads, which are the most expensive components, have had to be maintained.

Accordingly, there is a need for a modular shoulder prosthesis system which allows virtually complete flexibility of both tilt angle and radial offset adjustment while utilizing standard heads and stems.

SUMMARY OF THE INVENTION

The present invention provides a plurality of connectors for modular shoulder prostheses, which allow virtually complete flexibility with respect to tilt angle and radial offset adjustment, while utilizing standard heads and stems. By "standard heads and stems" it is meant that, for a given size of head and stem, i.e. a head having a given diameter and a stem having a given length and thickness, the complete range of tilt angle and radial offsets can be achieved with one "standard" head and one "standard" stem, as opposed to requiring a plurality of heads or stems of the given size.

As a result of the present invention's flexibility, the required inventory of prosthesis heads and stems can be greatly reduced. This is advantageous since the heads and stems are much more expensive components of a modular system than the connectors.

Also, if revision surgery needs to be performed, in order to modify a previously implanted prosthesis, the required adjustments can be carried out by changing connectors, without having to extract the stem from the humerus.

BRIEF DESCRIPTION OF THE DRAWINGS

FIG. 4 is an isometric view of an angled connector of the present invention.

FIGS. 5 and 6 are plan views showing possible orientations of the tilt-angle connector of the present invention.

FIG. 7 is a section view of the present invention utilizing an "offset" connector for providing a radial offset between the head and stem.

FIG. 8 is an isometric view of a radial offset connector of the present invention.

FIG. 9 is a plan view showing possible orientations of the radial offset connector of the present invention.

DESCRIPTION OF THE PREFERRED EMBODIMENTS

Figure 1:
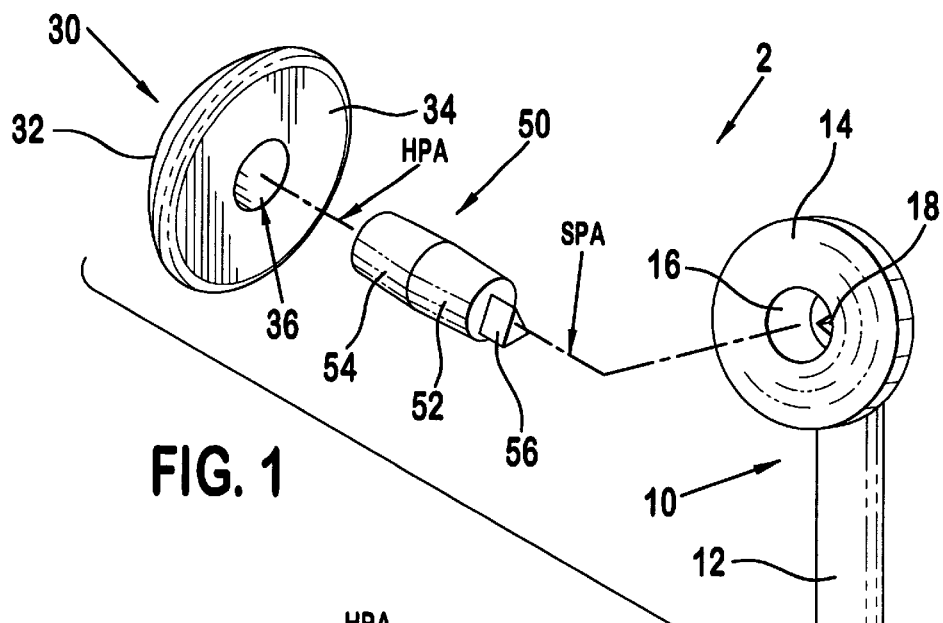
FIG. 1 is an isometric view of an embodiment of the present invention utilizing a "straight" connector between head and stem, i.e. one which provides neither a tilt angle nor a radial offset between those two components.

The preferred embodiments will be described with reference to the drawing figures where like numerals represent like elements throughout.

The shoulder prosthesis system 2 of the present invention is shown in FIG. 1 and comprises a stem 10, a head 30, and a plurality of connectors 50 (only one of which is shown). The stem 10 includes a shaft 12 having a lower end for insertion into the patient's humerus and an upper end which terminates in an angled face 14. The head 30 has a generally spherical convex surface 32 on one side and a generally flat surface 34 on the opposite side and is sized to fit in the patient's glenoid articular surface. The connectors 50 extend between the stem's angled face 14 and the head's flat surface 34 to fix the stem 10 and head 30 together. The components 10, 30, 50 are preferably manufactured from a metal material such as a cobalt chromium alloy, stainless steel, a titanium alloy or some other biocompatible material.

Figure 2:
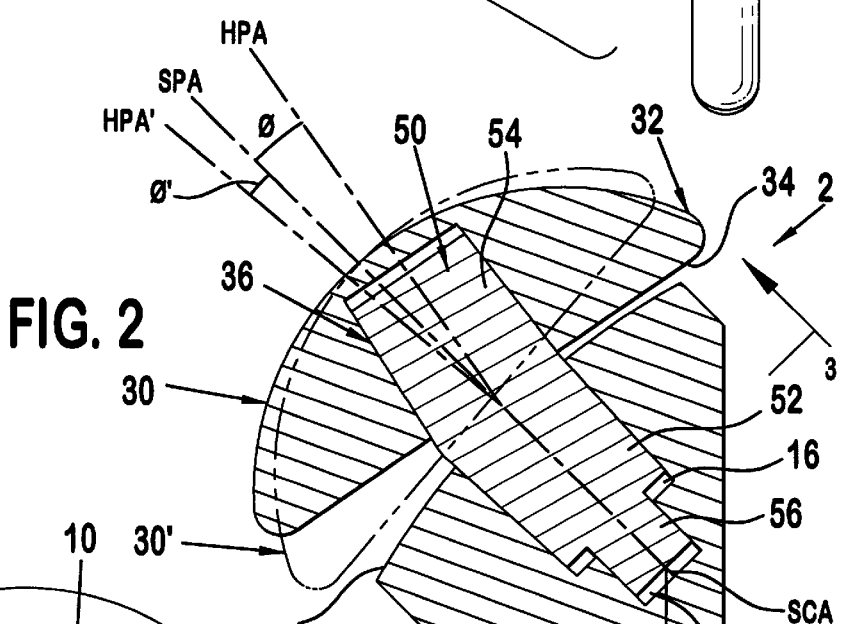
FIG. 2 is a section view of the present invention utilizing an "angled" connector for providing a tilt angle between the head and stem.

Referring to FIG. 2, the stem 10 will be described in more detail. A preferably conical cavity 16 extends from the face 14 into the stem 10 and is sized to receive a first projecting portion 52 of the connectors 50. The cavity 16 is preferably tapered inward to provide a Morse-taper fit between the stem 10 and the connectors 50. The stem cavity 16 is generally centered within face 14 and has an axis SCA which is preferably generally perpendicular to the face 14 and at an angle of, say, 135° with respect to the axis SA of shaft 12. The 135° angle is a common, natural inclination angle of the upper portion of a person's humerus and therefore requires relatively little adjustment with respect to head 30. Other angles may be selected and the difference compensated by means of the connectors 50.

Figure 3:
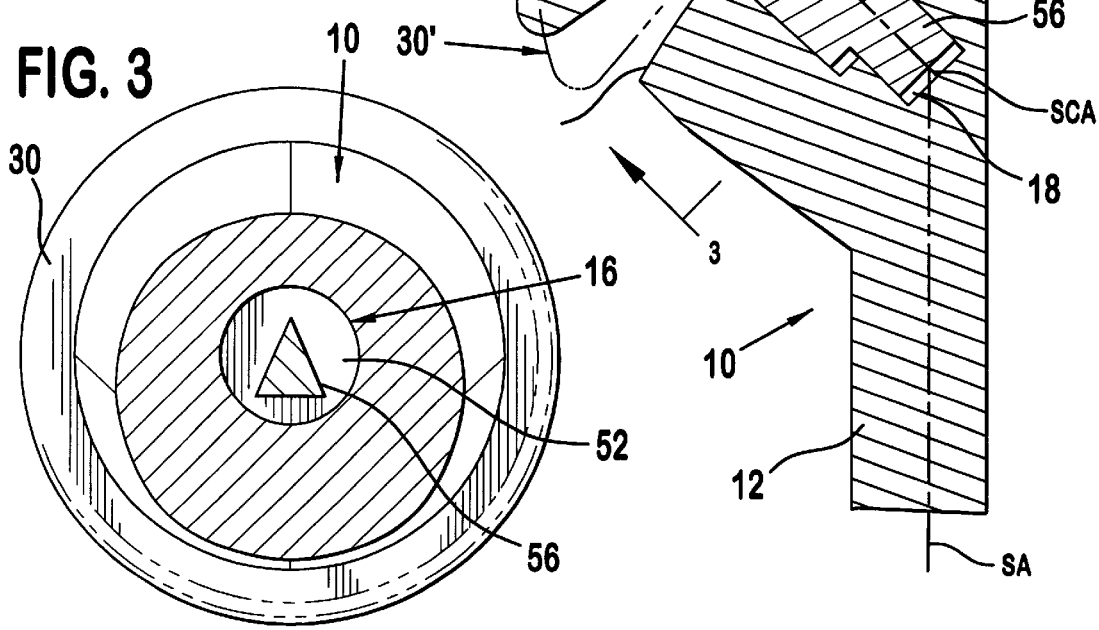
FIG. 3 is a section view taken along the line 3—3 in FIG. 2.

A keyway 18 extends from the cavity 16 into stem 10 and receives a connector key 56 to align the connector 50 in a proper orientation and to prevent rotation thereof. In the preferred embodiment shown in FIGS. 1 and 2, the keyway 18 extends beyond the bottom of the cavity 16. Alternatively, the keyway 18 can be positioned along the side wall of the cavity 16. In the preferred embodiment, the keyway 18 has an isosceles triangle cross-section. As shown in FIG. 3, each connector 50 has a matching triangular key 56 which can only be inserted in one orientation. This minimizes the chances of misalignment of a connector 50. In fact, once a particular connector 50 has been chosen, there is only one way in which it can be positioned in relation to stem 10 and therefore also only one way in which it orients head 30 relative to the stem.

Referring to FIGS. 1 and 2, the head 30 preferably has a conical cavity 36 generally centered within flat surface 34 and extending generally perpendicularly from the flat surface 34 into the head 30. Cavity 36 is preferably also tapered inward to provide a Morse-taper fit with a portion of the connector 50.

As shown in FIGS. 2 and 7, the system includes various connectors 50. Each connector 50 includes a projection 52 configured to mate with the stem cavity 16 and a projection 54 configured to mate with the head cavity 36. In the preferred embodiment, both stem and head projections 52 and 54 are tapered to provide the desired Morse-taper fit with the stem and head cavities 16 and 36 respectively. Upon insertion of the stem projection 52 into the stem cavity 16, the key 56 engages the keyway 18 and maintains the connector 50 in its desired orientation.

Referring to FIG. 1, a "straight" connector 50 is shown. For this component, the axis SPA of the stem projection 52 is coaxial with the axis HPA of the head projection 54 (see FIG. 2) in order to provide a generally straight connector 50. This straight connector 50 is utilized when the patient does not require any tilt angle or radial offset adjustment between the stem 10 and head 30. The lengths of the projections 52 and 54 may be varied from one connector 50 to another, enabling the head 30 to be spaced from the stem 10 as dictated by the patient's anatomy. For example, these lengths may vary in increments of 2 mm.

Referring to FIGS. 2 and 4, an angled connector 50 is shown. The head projection axis HPA is here at an obtuse angle $\phi$ relative to the stem projection axis SPA. This connector 50 is used when the patient's anatomy is such that the head 30 must be tilted relative to the stem 10 at an angle which is different from that (typically 135°) which exists between the upper end of stem 10 and its lower end inserted in the humerus. As shown in FIG. 2, the head projection axis HPA is at an angle $\phi$ relative to the stem projection axis SPA such that the head 30 is tilted slightly upward, for example to an angle of 140° in the same plane as that defined by the axis SCA and SA. The head 30', shown in phantom, is angled in the opposite direction, for example to an angle of 130°. The stem face 14 is preferably slightly convex to prevent interference with the outer edge of the flat surface 34 of head 30, when that head 30 is tilted at an angle as described above. Preferably, the surface 34 of head 30 may be made slightly concave for the same reason, namely to prevent interference with the outer edge of surface 14 when head 30 is tilted at an angle. Indeed, if the dimensions of the parts warrant it, both surfaces 34 and 14 may be made sufficiently curved to prevent such interference so that they do not impinge on each other at extreme tilt angles.

The angle $\phi$ of the connectors 50 can be any desired angle. However, to avoid the need for an excessive number of different connectors 50, the preferred system will include connectors having two angular inclinations of 5° each in each direction in the above-mentioned plane. Therefore, if the angle of the stem cavity axis SCA is 135° relative to the stem axis SA, the tilted angles of 125°, 130°, 140° and 145° can be provided by the preferred system using only four different tilt angle adjustment connectors 50. As shown in FIGS. 5 and 6, the preferred system will have connectors 50 which are configured to tilt the head up (FIG. 5—solid, line 54) or down (FIG. 5—broken line 54'). There will also be connectors 50 which are configured to tilt the head at right angles to the plane defined by axes SPA and SA, i.e. to the rear of the patient's shoulder (FIG. 6—solid line 54) or to the front (FIG. 6—broken line 54'). Other orientations are possible and contemplated, but since these directions of tilt adjustment are the most prevalent, a preferred system would only need adjustment in these four directions. Assuming that only 5° tilts are required in these front-and-rear directions, two more connectors 50 suffice to provide that added flexibility. The tilt orientation (i.e. up, down, front, rear) provided by each connector 50 will be determined by the orientation of the key 56 relative to the stem projection 52. In the preferred embodiment, wherein the keyway 18 is an isosceles triangle, each desired orientation of connector 50 will require a separate connector 50 with the key 56 positioned appropriately to enable the connector 50 to tilt the head 30 in the proper orientation. Each connector 50 will be marked, either directly or on its packaging, with its specific tilt angle and tilt direction. If the keyway 18 is multidirectional, a single connector 50 may be rotated into each of the desired orientations for the desired tilt angle $\phi$. In such an application, only the angular tilt, and not the direction, would need to be marked for each connector.

Turning to FIGS. 7 and 8, a connector 50 providing a radial offset for head 30 is shown. In these connectors 50, the head projection axis HPA is parallel to, but offset by a distance r from the stem projection axis SPA. As shown in FIGS. 7 and 9, the head 30 can be offset at various azimuthal positions along a radial path RP having a radius r. In the preferred embodiment, these radial offset connectors 50 are configured, by appropriate relative positioning of keys 56 and keyways 18, to provide eight possible offset positions (1–8) at 45° intervals in azimuth. Additionally, the distance r can be any desired distance. In the preferred embodiment, connectors 50 are provided which yield two different radial displacements r, of 2 mm and 4 mm respectively. Thus, the preferred system will include connectors 50 which provide radial offsets of either 2 or 4 mm at any one of the eight azimuth positions. Again, more or less flexibility can be provided by the use of greater or smaller numbers of connectors 50 at appropriate radial offsets and azimuth positions. Also, the radial offset connectors 50, or their containers, will be marked as to the offset distance and azimuth position which they provide.

Figure 10:
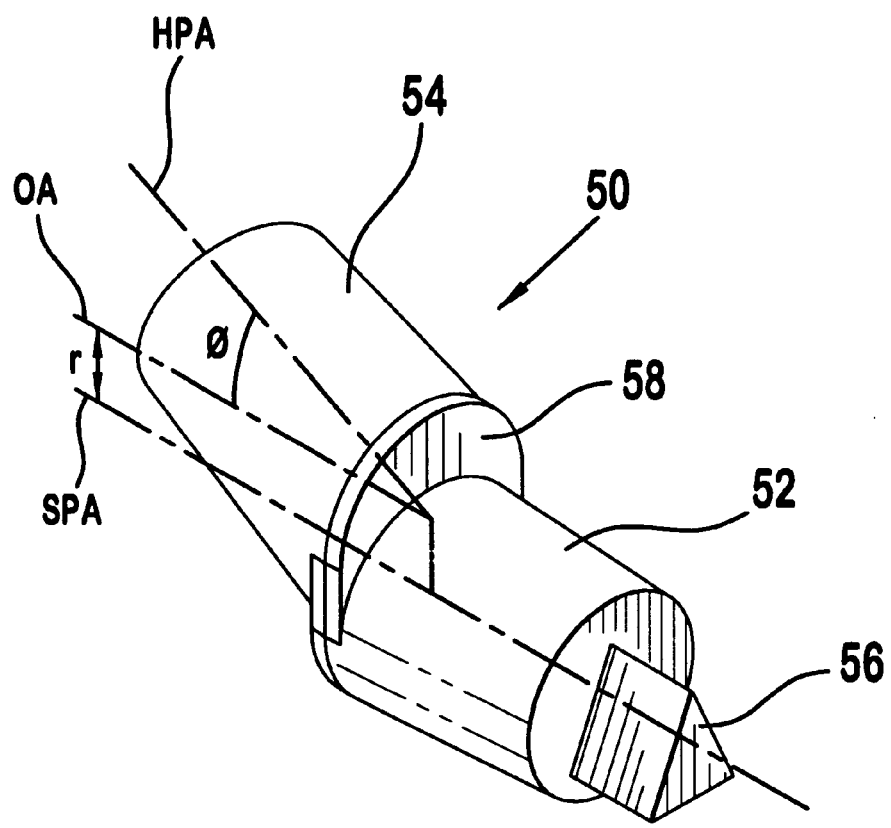
FIG. 10 is an isometric view of a combination tilt-angle and radial offset connector of the present invention.

Referring to FIG. 10, a connector 50 is shown that provides both tilt and radial offset adjustment for the head 30. The head projection axis HPA is offset a distance r, as indicated by the offset axis OA, and at an angle $\phi$ relative to the stem projection axis SPA. Such connectors 50 can be used when a patient's anatomy requires both tilt and radial offset adjustment.

As described above, one type of connector 50 (FIG. 1) provides "straight" connection; one type of connector 50 (FIGS. 2, 4, 5 and 6) provides tilt adjustment; another type (FIGS. 7, 8 and 9) provides radial offset adjustment; and another provides both tilt and radial adjustment (FIG. 10). Any or all types can have projections 52 and/or 54 of different lengths to provide different head-to-stem spacings. Collectively these types of connectors 50 enable the head 30 and stem 10 to be connected in virtually any desired relationship.

Having described the preferred components of the system 2, an example of their use will now be described.

To start, the size of the stem 10 and head 30 for the patient will be determined using known techniques. Next, the desired orientation (and spacing) between the selected stem 10 and the selected head 30 will be determined, again using known techniques.

Once these desired parameters are determined, the surgeon can simply select the appropriate connector 50 from the available set of connectors 50 which will provide these particular parameters.

If it is determined, for example, that there is required a radial offset of 2 mm, at an azimuth position of 45°, a tilt angle of 140°, and a stem-to-head spacing of 4 mm, the surgeon will select the connector 50 or connector package marked as such. This selected connector 50 will then be inserted in both the stem and head cavities 16 and 36 and the components tapped together to achieve the Morse-taper fit. The shoulder prosthesis is then ready for implant.

It will now be recognized that, except for their overall sizes, completely standard heads and stems can be used by the present invention, with all tilt angle, radial offset and spacing adjustments being provided by the connectors 50, which are much less expensive to inventory, thereby imparting to the present invention one of its exceptional advantages over the prior art.

What is claimed is:

1. A shoulder prosthesis system for implantation in a patient, said system having a stem with one end for inserting in the patient's humerus and having an angled face at its opposite end, a head for positioning in the patient's glenoid cavity having a generally spherical surface on one side and a generally flat face on the opposite side, a conical cavity in said stem face, a conical cavity in said flat head face, and a unitary member for connecting said head and stem having two projections extending in generally opposite directions, one projection being shaped for insertion in said stem cavity, the other for insertion in said head cavity, and said projections having axes which are radially offset from each other, and inclined at an obtuse angle to each other.

2. The shoulder prosthesis system of claim 1, wherein the cavity in the stem has an additional cavity forming a keyway and the projection shaped for insertion in the stem has a key shaped to mate with said keyway.

3. The shoulder prosthesis system of claim 1, wherein the connecting member is selected from a plurality of connecting members having different radial offsets and/or inclinations between their projection axes.

4. The shoulder prosthesis system of claim 1, wherein the stem and the head are each selected from a plurality of stems and heads, each having the respective cavities in the same location in the head face and in the stem face.

5. The shoulder prosthesis system of claim 3, wherein the different connecting members are all dimensioned so that their projections fit into the cavity in the same head and stem.

6. The shoulder prosthesis system of claim 1, wherein the projections are also conical and are so dimensioned as to provide a Morse-taper fit with the head and stem cavity, respectively.

7. The shoulder prosthesis system of claim 1, wherein the obtuse angles of different connecting members differ by 5° from each other.

8. The shoulder prosthesis system of claim 1, wherein the azimuths at which the radial offsets of different connecting members are located differ by 45° from each other.

9. A shoulder prosthesis system for implantation in a patient, said system having a stem with one end for inserting in the patient's humerus and having an angled face at its opposite end, a head for positioning in the patient's glenoid cavity having a generally spherical surface on one side and a generally flat face on the opposite side, a conical cavity in said stem face, a conical cavity in said flat head face, and a unitary member for connecting said head and stem having two projections extending in generally opposite directions, one projection being shaped for insertion in said stem cavity, the other for insertion in said head cavity, and said projections having axes which are either collinear, or parallel but radially offset from each other, or inclined at an obtuse angle to each other, the cavity in the stem having an additional cavity forming a keyway and the projection shaped for insertion in the stem having a key shaped to mate with said keyway, said stem and head being each selected from a plurality of stems and heads, each having the respective cavities in the same location in the head face and in the stem face, and the keyway in all said stems being in the same location relative to the stem cavity.

10. A shoulder prosthesis system for implantation in a patient, said system having a stem with one end for inserting in the patient's humerus and having an angled face at its opposite end, a head for positioning in the patient's glenoid cavity having a generally spherical surface on one side and a generally flat face on the opposite side, a conical cavity in said stem face, a conical cavity in said flat head face, and a unitary member for connecting said head and stem having two projections extending in generally opposite directions, one projection being shaped for insertion in said stem cavity, the other for insertion in said head cavity, and said projections having axes which are either collinear, or parallel but radially offset from each other, or inclined at an obtuse angle to each other, the cavity in the stem having an additional cavity forming a keyway and the projection shaped for insertion in the stem having a key shaped to mate with said keyway, said stem and head being each selected from a plurality of stems and heads, each having the respective cavities in the same location in the head face and in the stem face, the keyway in all said stems being in the same location relative to the stem cavity, and the key provided on different ones of said projections for insertion into the stem cavity being in different locations relative to the projections for connecting members with different offsets or inclinations.

11. A shoulder prosthesis system for implantation in a patient, said system having a stem with one end for inserting in the patient's humerus and having an angled face at its opposite end, a head for positioning in the patient's glenoid cavity having a generally spherical surface on one side and a generally flat face on the opposite side, a conical cavity in said stem face, a conical cavity in said flat head face, and a unitary member for connecting said head and stem having two projections extending in generally opposite directions, one projection being shaped for insertion in said stem cavity, the other for insertion in said head cavity, and said projections having axes which are either collinear, or parallel but radially offset from each other, or inclined at an obtuse angle to each other, and the radial offsets of different connecting members differing by 2 mm from each other.

12. A shoulder prosthesis system for implantation in a patient, said system having a stem with one end for inserting in the patient's humerus and having an angled face at its opposite end, a head for positioning in the patient's glenoid cavity having a generally spherical surface on one side and a generally flat face on the opposite side, a conical cavity in said stem face, a conical cavity in said flat head face, and a unitary member for connecting said head and stem having two projections extending in generally opposite directions, one projection being shaped for insertion in said stem cavity, the other for insertion in said head cavity, and said projections having axes which are either collinear, or parallel but radially offset from each other, or inclined at an obtuse angle to each other, the face of at least one of the head and stem is sufficiently curved to prevent said faces from touching when inclined relative to each other by a connecting member having projections at a given obtuse angle.

13. A shoulder prosthesis system for implantation in a patient, said system having a stem with one end for inserting in the patient's humerus and having an angled face at its opposite end, a head for positioning in the patient's glenoid cavity having a generally spherical surface on one side and a generally flat face on the opposite side, a conical cavity in said stem face, a conical cavity in said flat head face, and a unitary member for connecting said head and stem having two projections extending in generally opposite directions, one projection being shaped for insertion in said stem cavity, and the other for insertion in said head cavity, and said projections having axes which are radially offset from each other.

* * * * *